United States Patent
Naumann

(10) Patent No.: US 7,713,481 B2
(45) Date of Patent: May 11, 2010

(54) AUTOMATIC PIPETTING UNIT WITH REPLACEABLE PIPETTING HEAD

(75) Inventor: Uwe Naumann, Jena (DE)

(73) Assignee: CyBio AG, Jena (DE)

( * ) Notice: Subject to any disclaimer, the term of this patent is extended or adjusted under 35 U.S.C. 154(b) by 318 days.

(21) Appl. No.: 12/013,960

(22) Filed: Jan. 14, 2008

(65) Prior Publication Data

US 2008/0170965 A1 Jul. 17, 2008

(30) Foreign Application Priority Data

Jan. 17, 2007 (DE) .................... 20 2007 000 904 U

(51) Int. Cl.
*B01L 3/02* (2006.01)
*G01N 1/00* (2006.01)
(52) U.S. Cl. ................. 422/100; 73/864.24; 73/864.25; 436/54; 422/63
(58) Field of Classification Search ................. 422/100; 73/864.14, 864.24
See application file for complete search history.

(56) References Cited

U.S. PATENT DOCUMENTS

| | | | |
|---|---|---|---|
| 6,325,114 B1 * | 12/2001 | Bevirt et al. ................. | 141/130 |
| 6,846,680 B2 | 1/2005 | Friswell et al. | |
| 6,982,063 B2 * | 1/2006 | Hamel et al. ................. | 422/100 |
| 7,541,001 B2 * | 6/2009 | Kraemer et al. .............. | 422/65 |
| 2001/0039843 A1 * | 11/2001 | Schoeppe ................ | 73/863.32 |

FOREIGN PATENT DOCUMENTS

| | | |
|---|---|---|
| WO | 02/096562 A1 | 12/2002 |
| WO | 2006/123690 A1 | 11/2006 |

OTHER PUBLICATIONS

"CyBi-Well vario 96 and 384 Channel Simultaneous Pipettor", in Internet: http://www.cybio-ag.com/en/Products/CyBi_Well_vario/site_196/.
"Automated Pipetting Systems", in Internet: http://www.matrixtechcorp.com/automated/pipetting.aspx?id=72.

* cited by examiner

*Primary Examiner*—Brian J Sines
*Assistant Examiner*—Jennifer Wecker
(74) *Attorney, Agent, or Firm*—Duane Morris LLP

(57) ABSTRACT

The invention concerns an automatic pipetting unit with a replaceable pipetting head. The pipetting head includes two head rails located on opposite sides. The pipetting unit also has two horizontal guide channels located in the interior of the pipetting unit for supporting the two head rails. Two frame-mounted, double-sided slider crank mechanisms are vertically arranged in the pipetting unit. Each double-sided slider crank mechanism includes two crank mechanisms each connected to a common articulated thrust joint by a thrust couple. The horizontal guide channels are formed in the articulated thrust joint and the crank mechanisms are connected indirectly to a head cover of the pipetting unit, so that with the opening and closing motion of the head cover the two slider crank mechanisms are moved between two end positions so that the pipetting head can be moved vertically between a lower end working position and an upper end replacement position.

3 Claims, 7 Drawing Sheets

AUTOMATIC PIPETTING UNIT WITH REPLACEABLE PIPETTING HEAD

Automatic pipetting units are used in particular in applications in laboratories where liquid substances in minute quantities are to be dispensed into individual vessels of a set of vessels, or when such quantities are to be removed and dispensed into individual vessels of another set of vessels. For a high efficiency of laboratory processes, it is desirable—and for uniform test conditions in all individual vessels it is indispensable—that all individual vessels be filled with a single dispensing step. For this purpose, the pipetting head of the automatic pipetting unit is designed so that it has the same number of pipetting tips as there are individual vessels, and the pipetting tips are arranged at the same grid spacing with respect to each other as are the midpoints of the individual vessels.

Some typical vessel arrays can be, for example, microtiter plates. The individual vessels are formed by wells, which are arranged in an 8×12, 16×24 or 32×48 grid, for instance. The outer dimensions of the microtiter plates are standardized, that is, they are the same, regardless of the number of wells. Therefore, as the number of the wells increases and the grid spacing becomes smaller, the wells must be designed with increasingly smaller interior dimensions. The necessity for a precise alignment of the well centers and of the axes of the pipette tips to each other increases, so that an exact liquid dispensing into the individual wells will occur, or so that the pipette tips will enter the wells at all in a 32×48 grid. This alignment will occur when both the vessel array and also the pipetting head are aligned to a common reference basis in the automatic pipetting unit.

In the case of automatic pipetting units which are delivered from the manufacturer with a non-replaceable pipetting head, the alignment of the pipetting head in the automatic pipetting unit is effected by a one-time adjustment during assembly, and then locking in place.

In order to be able to adapt an automatic pipetting unit in a flexible manner to different vessel arrays, it is sold with several pipetting heads compatible with automatic pipetting units, and these heads must be replaced by the user himself. Special operating steps must be taken so that the different pipetting heads can be easily replaced with little effort, and the new pipetting head is aligned automatically without the need for a renewed adjustment to the reference basis.

Equipment with this kind of functionality is already known in the state of the art.

For example, the Zeiss-Sumal model AD96 produced in the year 1986 had a somewhat cumbersome method for replacement of pipetting heads. The user had to employ a special tool to do so.

Starting in 1993 the German firm of Jenoptron GmbH produced and marketed its series 96 simultaneous pipetting unit IGEL with electromotor-based and microcontroller monitored pipette head replacement unit.

In the recent document WO 02/096562 an automatic pipetting unit with a replaceable pipetting head is disclosed. The replacement of this pipetting head is described by reference to the description of the installation and locking processes with the aid of FIGS. 16, 16A and 20 of document WO 02/096562. Removal takes place accordingly in the reverse order.

In order to install the pipetting head 600 and to lock it into the automatic pipetting unit 500, the coupling plate 514 (FIG. 16) to which the pipetting head 600 is attached must be accessible from two sides, that is, the automatic pipetting unit 500 must be open on these two sides. Via one of the open sides, the pipetting head 600 is inserted horizontally into its subsequent working plane below the coupling plate 514 on two lateral guide rails 608 up to the stops 616 (FIG. 16A), in order to bring it into its working position. Next, the pipetting head 600 is secured to the coupling plate 514 by means of four attachment elements 620. The attachment elements 620 illustrated in FIG. 16 pertain to knurled screws which are pivotably mounted in pairs opposite each other at the longitudinal sides of the pipetting head 600 in a plunger retaining plate 602 of the pipetting head 600. The knurled screws 620 are brought into a vertical position and thus engage with the coupling plate 514 by means of elongated holes 515 open on one side. When the knurled screws 620 are installed, the pipetting head 600 is clamped to the coupling plate 514 of the plunger drive unit.

The disadvantages of this kind of design are—
- the necessity for access to all knurled screws 620 from two sides of the automatic pipetting unit 500,
- the required open space in front of the automatic pipetting unit 500 in the working plane of the pipetting head 600, since it can only be removed at this level, even though it is precisely this space which is used by the increasingly more commonly used devices for inserting pipette tips 702 into their holder 710,
- the transverse forces which in the long term destroy the seal between plunger 652 and gasket 662 (FIG. 20), which necessarily occur when inserting and extracting the pipetting head 600 between its fixed plates 604/606 and the moving plunger retaining plate 602, and
- the four attachment elements 620 which must each be tightened and loosened.

The present invention is based on the problem of finding a constructive design for an automatic pipetting unit allowing the pipetting head to be easily and quickly replaced.

This problem is solved for an automatic pipetting unit according to the present invention.

The invention will be described in greater detail below based on the illustrations with reference to one exemplary embodiment. In the figures.

Figure 1A:
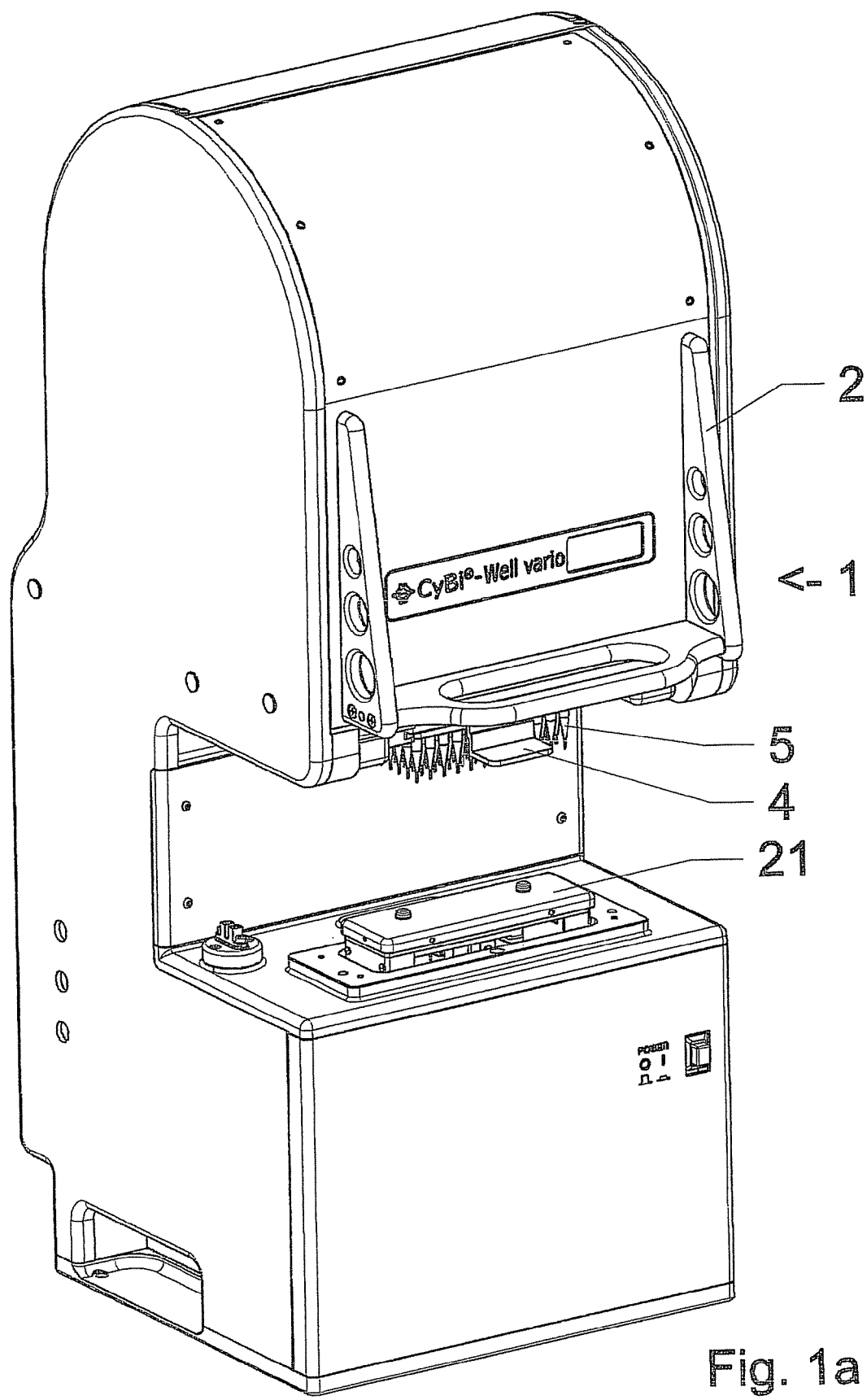
FIG. 1a is a perspective view illustrating an automatic pipetting unit ready for use.

FIG. 1a illustrates an example of automatic pipetting unit 1 according to the present invention as it appears in an operational state. Head cover 2 is located in the upper housing area. A pipetting head 3 (FIG. 1b) is housed behind the head cover 2, whereas an opening for a tip magazine 4 remains. Tip magazine 4 of pipette tips 5 can be pushed into the opening in order to be pressed against a sealing surface located at the underside of the pipetting head 3 by means of a pressing mechanism.

Figure 1B:
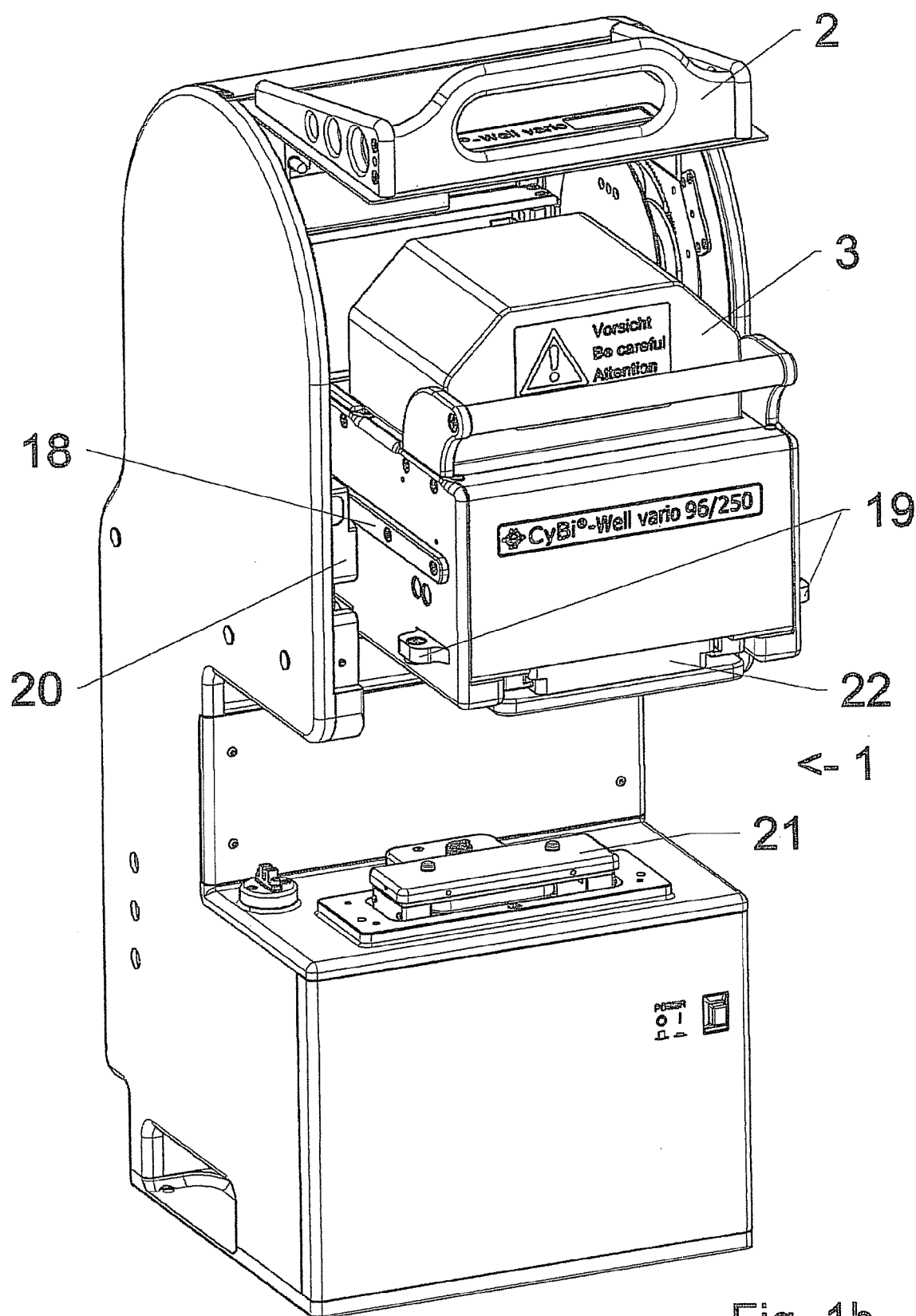
FIG. 1b is a perspective view illustrating the automatic pipetting unit according to FIG. 1a with its head cover opened and pipetting head pulled-out.

FIG. 1b shows the head cover 2 open and the pipetting head 3 is shown as already half removed from the housing of the automatic pipetting unit 1. In order to remove the pipetting head 3, the tip magazine 4 which is locked to the pipetting head 3, is replaced by a head changing tool 22. This tool is used to protect the sealing surface during placement of the pipetting head 3 outside of the automatic pipetting unit 1, as a handle for lowering during removal and installation, and as a support surface for setting down the removed pipetting head 3.

When the head cover 2 is either fully closed or fully opened, the pipetting head 3 is located at a respective end position of its travel path. These end positions are, with the head cover 2 closed the working position (lower end position), and with the head cover 2 open the replacement position (upper end position).

In the working position, the pipetting head 3 is located in a horizontally defined position with respect to the hoisting table 21 located underneath it and integrated into the automatic pipetting unit 1. The hoisting table 21 is designed so that a vessel array positioned thereon, e.g., a microtiter plate, is aligned with respect to the pipette tips 5 so that their axes are incident on the centers of wells.

In the replacement position, the pipetting head 3 is elevated in a vertical direction with respect to the working position. During the elevation, the pipetting head 3 is automatically released from its mechanical adjustment with respect to the automatic pipetting unit 1, and its electrical connection to the automatic pipetting unit 1 is broken. It can then be removed from the automatic pipetting unit 1 at a position higher than the working position, so that the free space required for replacement of the pipetting head 3 can be reduced compared to prior known systems. That is, in particular, any apparatus located in front of the automatic pipetting unit 1—such as an automatic tip replacement unit for replacement of a tip magazine 4 with used pipette tips 5 by a tip magazine 4 with unused pipette tips 5—can remain in place during replacement of the pipetting head 3.

The automatic pipetting unit 1 has a hoisting device for hoisting and lowering of the pipetting head 3 between the replacement setting and the working position. The hoisting device is composed of two double-sided, frame-mounted, slider crank mechanisms which are connected together by means of a head cover support 12 to which the head cover 2 is attached.

Figure 3A:
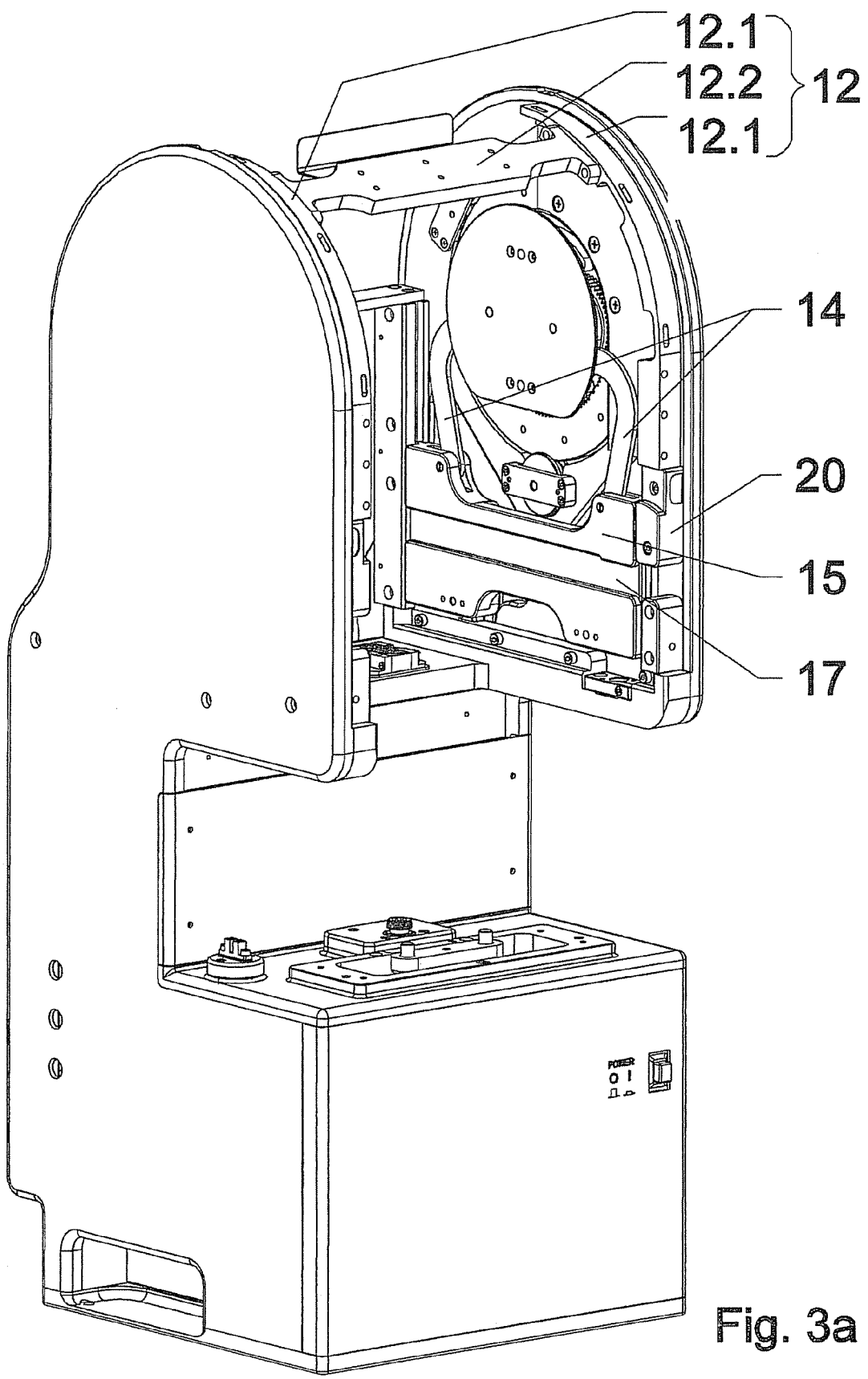
FIG. 3a is a perspective view illustrating the automatic pipetting unit according to FIG. 1a, partly without the enclosure.

As is shown in FIG. 3a at one of the two slider crank mechanisms, these units are each housed at the side walls in the automatic pipetting unit 1.

Figure 2A:
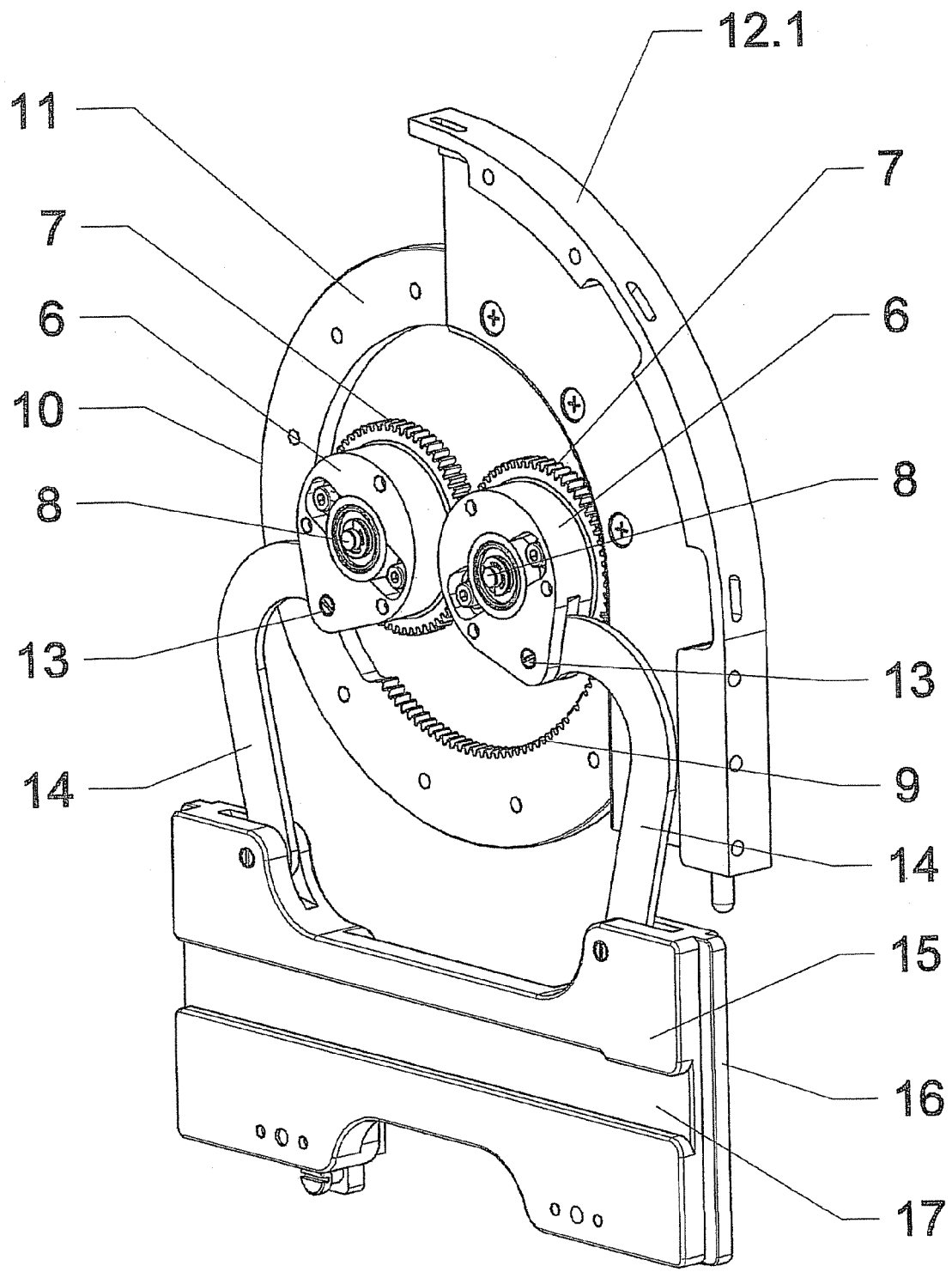
FIG. 2a is a perspective view illustrating the slider crank mechanism of the automatic pipetting unit according to FIG. 1 in the working position of the pipetting head, as viewed from the inside of the unit.
Figure 2B:
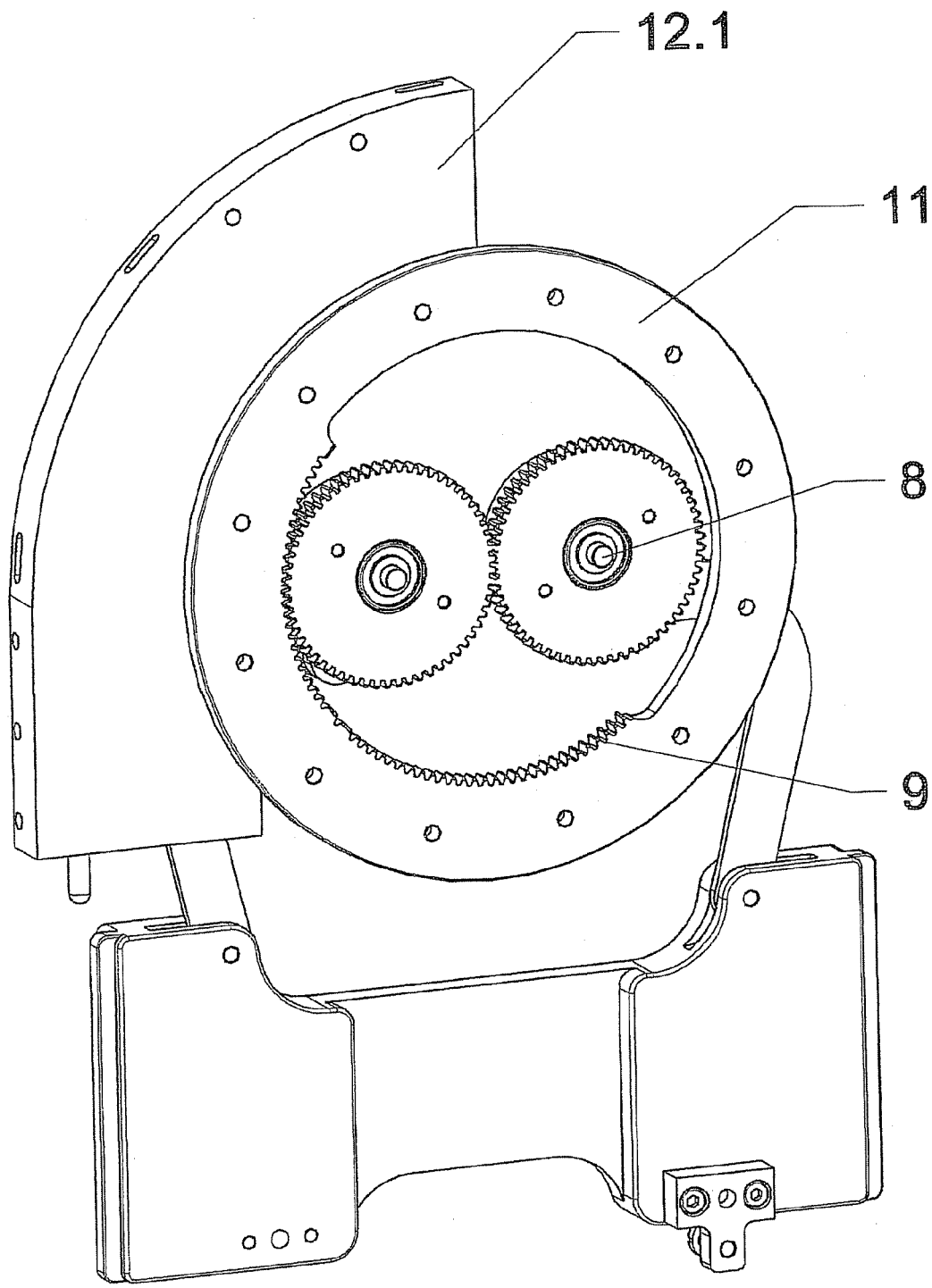
FIG. 2b is a perspective view illustrating the slider crank mechanism of the automatic pipetting unit according to FIG. 1 in the working position of the pipetting head, as viewed from the outside of the unit through the right side wall.
Figure 2C:
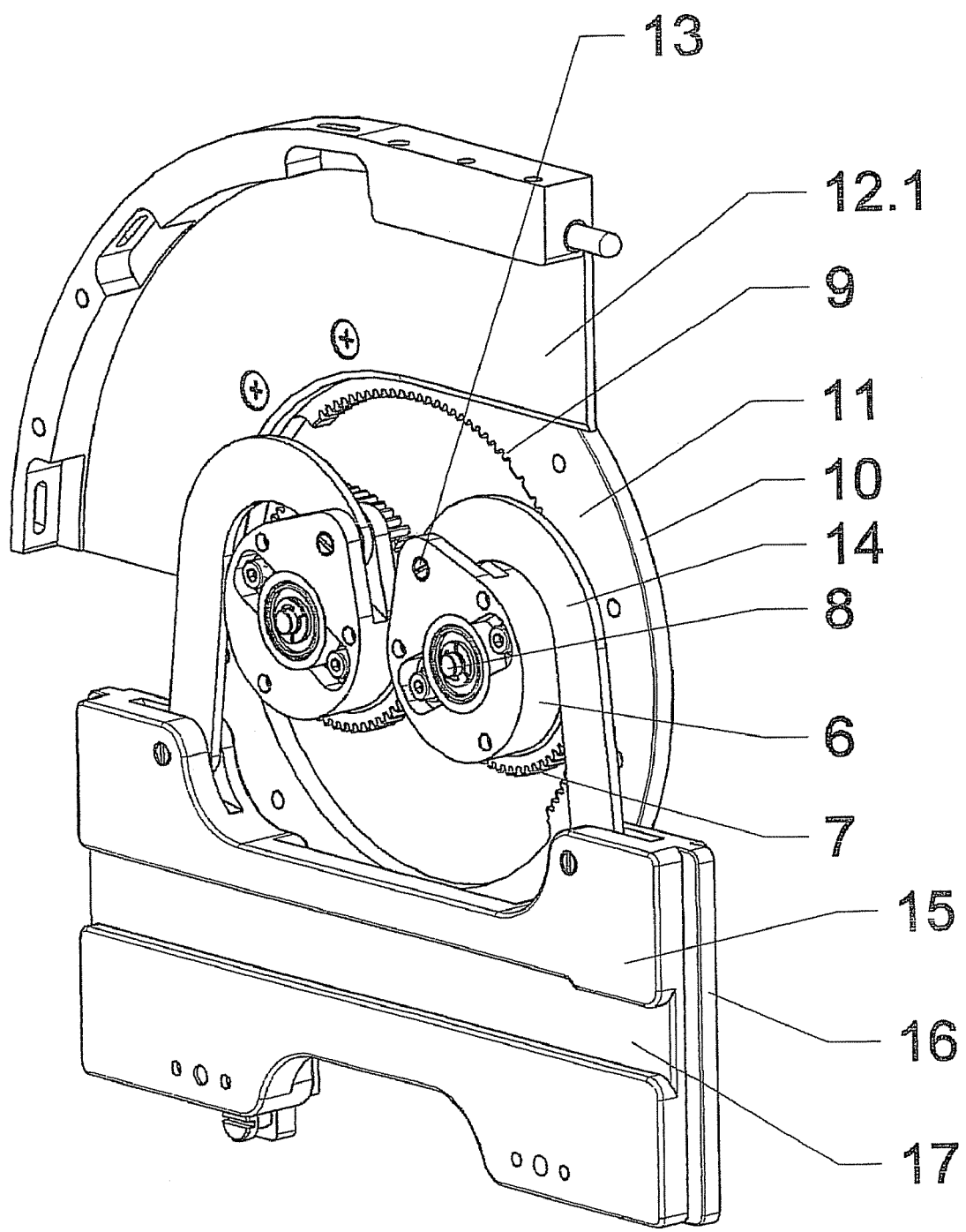
FIG. 2c is a perspective view illustrating the slider crank mechanism of the automatic pipetting unit according to FIG. 1 in the replacement position of the pipetting head, as viewed from the inside of the unit.

Referring to FIGS. 2a-2c, a double-sided slider crank mechanism is composed of two crank mechanisms 6 each with a circumferential outer toothing 7 that engage with each other. The crank mechanisms 6 are each frame mounted by means of a pivot 8 and are positioned within an internal gear so that one of the two outer toothings 7 engages with an interior tooth segment 9 of internal gear 10.

The crank mechanisms 6 are each connected to one end of a thrust couple 14 by means of a rotary joint 13 located at the perimeter of the crank mechanism 6. The other end of the thrust couple is connected to a common articulated thrust joint 15. The articulated thrust joint 15 is moved vertically by means of two lateral guide rails 16 in and between two guide elements 20 (see FIGS. 3a and 3b). A guide channel 17 is formed in the articulated thrust joint 15 on the side surface facing away from the housing. Channel 17 is provided to hold the pipetting head 3.

Figure 3B:
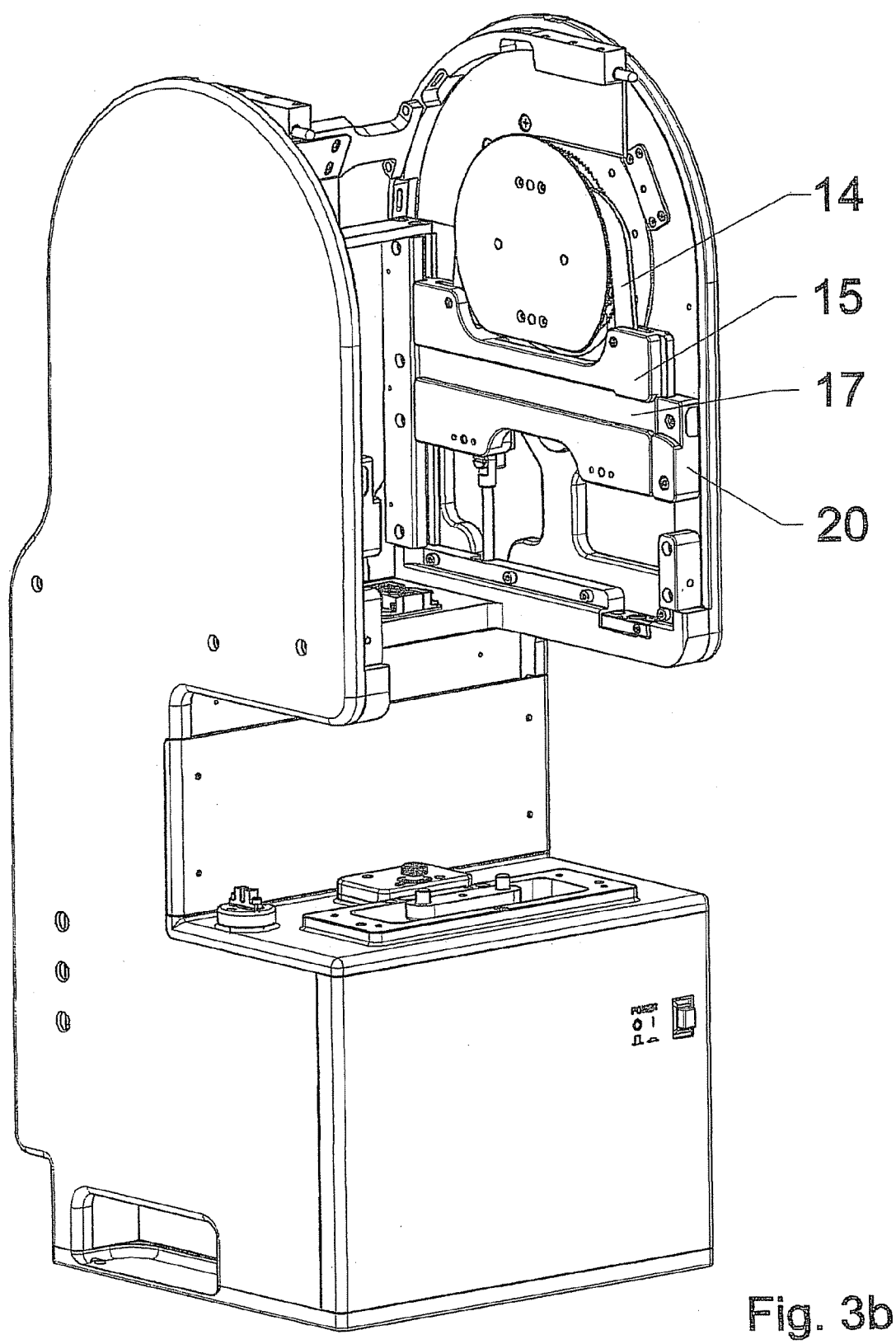
FIG. 3b is a perspective view illustrating the automatic pipetting unit according to FIG. 1b, partly without the enclosure.

Referring to FIGS. 3a and 3b, the two double-sided slider crank mechanisms are rigidly connected together by means of the head cover support 12. The head cover support 12 consists of two support sides 12.1 and one support bar 12.2 that rigidly connects the two support sides 12.1 together at a spacing greater than the width of the pipetting head 3. The two support sides 12.1 are each attached to one inner, front surface 11 of each internal gear 10.

The mode of operation of the hoisting device will be explained in greater detail below based on the operational use of a pipetting head 3 in the automatic pipetting unit 1.

As illustrated in FIG. 1b, the head cover 2 is open and the hoisting unit is in the replacement position, as indicated in FIGS. 2c and 3b. The articulated thrust joint 15 is located in its upper end position in which the pipetting head 3 is introduced into the two guide channels 17 by means of lateral head rails 18.

In order also to be able to introduce two lugs 19 formed on the side of the pipetting head 3 and provided for self-adjustment of the pipetting head 3, unhindered into the interior of the automatic pipetting unit 1, an appropriate open space must be provided beneath the guide element 20.

In order to hold the hoisting device or the hoisting device with inserted pipetting head 3 in the replacement position against the force of gravity, stationary permanent magnets are provided on which, in this end position, the hoisting device is held after attraction of the head cover support 12.

After complete insertion of the pipetting head 3, the head cover 2 is closed by manually cancelling the attraction force of the permanent magnet—already compensated in part by the weight of the pipetting head 3—by a short downward movement of the head cover 2.

With closure of the head cover 2, which is connected rigidly to the two internal gears 10 via the head cover support 12, the movement of the head cover 2 is transferred directly to the two internal gears 10. The inner tooth segments 9 of the internal gears 10 are rolled onto the outer toothing 7 of the crank mechanisms 6 facing the cover opening, and cause them to begin a rotating motion. At the same time, the other crank mechanisms 6 are caused to rotate in the opposite direction and the articulated thrust joints 15 connected to the crank mechanisms 6 are lowered by means of the thrust couples 14. This lowering takes place automatically due to the inherent weight of the pipetting head 3 and is decelerated by means of dampers located on both sides between the articulated thrust joints 15 and the frame, so that the pipetting head 3 will be lowered gently into its working position (lower end position).

In this lower end position the pipetting head 3 automatically assumes a defined position in the automatic pipetting unit 1 and thus also with respect to the hoisting table 21 in which the pipetting head 3 is held in place due to its own weight—by means of ball elements located on the lugs 19 and a third ball element located on the pipetting head 3, with a three-point contact defined by a conical recess, a U-shaped channel, and a plane, without having to be adjusted and locked. At the same time, the electrical connection between pipetting head 3 and automatic pipetting unit 1 is established automatically.

After the insertion of the pipetting head 3 into the automatic pipetting unit 1, the head cover 2 must be closed—this step is needed anyway—in order to bring the pipetting head 3 into its working position and to keep it there.

Accordingly, for the removal process, the head cover 2 has to be opened completely and the pipetting head 3 can be removed without any other attachment elements having to be loosened.

The ordinary technician skilled in the field of this invention will see that the invention is not limited to the details of the sample embodiments presented above, but rather that the present invention can be embodied in other special formats, without departing from the scope of the invention, which is otherwise specified by the attached claims.

EXPLANATION OF SYMBOLS

1 Automated pipetting unit
2 Head cover
3 Pipetting head
4 Tip magazine
5 Pipetting tips
6 Crank mechanism
7 Outer toothing
8 Pivot
9 Tooth segment
10 Internal gear
11 Front surface
12 Head cover support
12.1 Support side
12.2 Support bar
13 Rotary joint
14 Thrust couple
15 Articulated thrust joint
16 Guide rail
17 Guide channel
18 Head rail
19 Lug
20 Guide element
21 Hoisting table
22 Head changing tool

The invention claimed is:

1. An automatic pipetting unit with a replaceable pipetting head, comprising a pipetting head; two head rails located on opposite sides of said pipetting head; two horizontal guide channels located in the interior of said pipetting unit for supporting said head rails; a frame; two frame-mounted, double-sided slider crank mechanisms, frame-mounted by means of a pivot and positioned within an internal gear, and vertically arranged in said pipetting unit; each double-sided slider crank mechanism including two crank mechanisms each connected to a common articulated thrust joint by a thrust couple; said horizontal guide channels being formed in said articulated thrust joint and said crank mechanisms being connected indirectly to a head cover of said pipetting unit; so that with the opening and closing motion of said head cover said two slider crank mechanisms are moved between two end positions so that the pipetting head can be moved vertically between a lower end working position and an upper end replacement position.

2. The automatic pipetting unit according to claim 1, characterized in that the two slider cranks of the particular slider crank mechanism each have an outer toothing which engages with the other and are each engaged with an inner gear segment of an internal gear, and the internal gears are rigidly connected to the head cover by means of a head cover support.

3. The automatic pipetting unit according to claim 2, characterized in that the pipetting head, due to its inherent weight, is positioned by means of a three-point contact defined by a conical recess, a U-shaped channel, and a plane, without having to be adjusted and locked in a defined position in the automatic pipetting unit in its working position.

* * * * *